US007660380B2

(12) United States Patent
Boese et al.

(10) Patent No.: US 7,660,380 B2
(45) Date of Patent: Feb. 9, 2010

(54) METHOD FOR CORRECTION OF TRUNCATION ARTIFACTS IN A RECONSTRUCTION METHOD FOR TOMOGRAPHIC IMAGING WITH TRUNCATED PROJECTION DATA

(75) Inventors: Jan Boese, Eckental (DE); Bernhard Scholz, Heroldsbach (DE)

(73) Assignee: Siemens Aktiengesellschaft, Munich (DE)

( * ) Notice: Subject to any disclaimer, the term of this patent is extended or adjusted under 35 U.S.C. 154(b) by 2 days.

(21) Appl. No.: 12/221,423

(22) Filed: Jul. 31, 2008

(65) Prior Publication Data
US 2009/0034817 A1  Feb. 5, 2009

(30) Foreign Application Priority Data
Aug. 3, 2007  (DE)  ........................ 10 2007 036 561

(51) Int. Cl.
*A61B 6/03* (2006.01)
(52) U.S. Cl. .............................................. 378/4; 378/18
(58) Field of Classification Search .................... 378/4, 378/18; 382/128–131
See application file for complete search history.

(56) References Cited

U.S. PATENT DOCUMENTS

| | | | | |
|---|---|---|---|---|
| 6,307,909 | B1* | 10/2001 | Flohr et al. ..................... | 378/4 |
| 6,574,296 | B2* | 6/2003 | Stierstorfer ................... | 378/15 |
| 7,254,259 | B2* | 8/2007 | Hsieh et al. .................. | 382/131 |
| 2002/0186809 | A1* | 12/2002 | Flohr et al. ..................... | 378/4 |
| 2004/0066909 | A1* | 4/2004 | Lonn et al. ................... | 378/901 |
| 2004/0066911 | A1 | 4/2004 | Hsieh et al. | |
| 2006/0120507 | A1 | 6/2006 | Brunner et al. | |
| 2006/0262894 | A1* | 11/2006 | Bernhardt et al. ............. | 378/4 |
| 2008/0123806 | A1* | 5/2008 | Scholz .......................... | 378/18 |
| 2008/0165918 | A1* | 7/2008 | Scholz ........................... | 378/4 |

FOREIGN PATENT DOCUMENTS

DE   103 45 705 A1   9/2004

OTHER PUBLICATIONS

Beyer et al., Whole-Body 18F-FDG PET/CT in the Presence of Truncation Artifacts, Jan. 2006, The Journal of Nuclear Medicine, vol. 47, No. 1, pp. 91-99.*

(Continued)

*Primary Examiner*—Edward J Glick
*Assistant Examiner*—John M Corbett

(57) ABSTRACT

There is described a method for correction of truncation artifacts in reconstructed tomographic images in a reconstruction method for tomographic images with truncated projection image data in the reconstructed tomographic images, in which divergent radiation is emitted from a radiographic source, an object to be examined is x-rayed with the divergent radiation in different projection directions, the radiation penetrating through the object to be examined is detected by a detector as projection images, with the data of the signal being arranged in a number of projection data rows and projection images detected by the detector being expanded line-by-line through extrapolation of the projection data rows. In this case the signal of a projection data row can be smoothed with a polynomial filter to reduce the noise component of the signal and the truncated proportion of the projection data row can be computed from the smoothed signal of the projection data row by means of an extrapolation method, with the extrapolation widths being derived from a number of rows.

20 Claims, 5 Drawing Sheets

OTHER PUBLICATIONS

You et al., FBP algorithms for attenuated fan-beam projections, May 13, 2005, Inverse Problems, vol. 21, pp. 1179-1192.*

Zellerhoff et al., Low contrast 3D-reconstruction from C-arm data, Published online Aug. 30, 2005, SPIE vol. 5745, pp. 646-655.*

Scholtz et al., Correction of Truncation Artifacts in C-arm CT Images by Fan-Beam Extrapolation Using Savitzky-Golay Filter, Dec. 2, 2008, RSNA 2008, Presentation Code: SSJ24-06.*

You, ReconAnalytical Class Reference, Copyright 2003-2005, available at http://www.cubic-imaging.com/CodeDoc/ImageRecon/class_recon_analytical.html.*

Lascu et al., Electrocardiogram Compression and Optimal ECG Filtering Algorithms, Apr. 2008, WSEA Transactions on Computers, Issue 4, vol. 7, pp. 155-164.*

Press et al., Numerical Recipes in C. The Art of scientific Computing, 2002, Second Edition, Second Edition, ISBN 0-512-43108-5, Chapter 14.8 Savitzky-Golay Smoothing Filters, pp. 650-655.*

Savitzky et al., Smoothing and Differentiation of Data by Simplified Least Squares Procedures, Jul. 1964, Analytical Chemistry, vol. 36, No. 8, pp. 1627-1639.*

B. Ohnesorge, T. Flohr, K. Schwarz, J. P. Heiken, K T. Bae; "Efficient correction for CT image artifacts caused by objects extending outside the scan field of view"; Am. Assoc. Phys. Med.; Med. Phys. vol. 27, No. 1; Jan. 2000; pp. 39-46.

Katia Sourbelle, Marc Kachelrieβ, Willi A. Kalender; "Reconstruction from Truncated Projections in Cone-Beam CT using Adaptive Detruncation"; Paper #1506; RSNA 2003; pp. 1-3.

Christian Penβel, Marc Kachelrieβ, Katia Sourbelle, Willi A. Kalender; "Hybrid Detruncation (HDT) Algorithm for the Reconstruction of CT Data"; RSNA 2004; pp. 1-18; Institute of Medical Physics University of Erlangen-Nürnberg, Germany.

J. Hsieh, E. Chao, J. Thibault, B. Grekowicz, A. Horts S. Mc Olash, T.J. Myers; "A novel reconstruction algorithm to extend the CT scan field-of-view"; Am. Assoc. Phys. Med.; Med. Phys. vol. 31, No. 9; Sep. 2004; pp. 2385-2391.

Jared Starman; "Extrapolating Truncated Projections Using $0^{th}$ and $1^{st}$ Moment Constraints"; Nov. 28, 2004; pp. 1-2.

* cited by examiner

METHOD FOR CORRECTION OF TRUNCATION ARTIFACTS IN A RECONSTRUCTION METHOD FOR TOMOGRAPHIC IMAGING WITH TRUNCATED PROJECTION DATA

CROSS REFERENCE TO RELATED APPLICATIONS

This application claims priority of German application No. 10 2007 036 561.8 DE filed Aug. 3, 2007, which is incorporated by reference herein in its entirety.

FIELD OF INVENTION

The invention relates to a method for correction of truncation artifacts in the reconstructed tomographic images in a reconstruction method for tomographic images with truncated projection image data, in which divergent radiation is emitted from a radiographic source, an object to be examined is x-rayed with the divergent radiation in different projection directions, the radiation penetrating through the object to be examined is detected by a detector as projection images, with the data of the signal being arranged in a number of projection data rows and projection images detected by the detector being expanded row-by-row through extrapolation of the projection data rows.

BACKGROUND OF INVENTION

An x-ray diagnostic device of this type, known for example from US 2006/0120507 A1, is shown in FIG. 1. The x-ray diagnostic device features a C-arm 2 supported to allow it to rotate on a stand 1, with an x-ray source, for example an x-ray emitter 3, and an x-ray detector 4, being accommodated on the ends of said arm.

SUMMARY OF INVENTION

The x-ray detector 4 can be a rectangular or square semiconductor detector which is preferably made of amorphous silicon (aSi).

In the path of the x-ray radiation source 3 is a patient support table 5, for recording images of the heart or a patient under examination for example. An imaging system 6, which receives and processes the image signals of x-ray image detector 4, is connected to the x-ray diagnostic device. The x-ray images can then be viewed on a monitor 7.

When tomographic images are being recorded, it can now occur that the object for which the image is to be recorded extends beyond the measuring field area. in this case the measured projection data is identified as cut off or truncated.

This is now explained with reference to FIG. 2, which shows a view in an axial direction onto the trajectory 10 of the beam focus 11 of the x-ray source 3 as well as trajectory 12 of a small x-ray image detector 4' or of a large x-ray image detector 4" around an object 13 to be examined.

The small x-ray image detector 4' can for example measure 17.5×17.5 $cm^2$ and the size of the large x-ray image detector 4" can be 29.5×36.0 $cm^2$. The object to be examined 13 can for example be the body of an animal or of a human being, but can also involve a phantom body, which for example can have a height of 26 cm and a width of 37 cm.

The x-ray source 3 emits an x-ray beam 14' or 14" emanating from the x-ray focus 11, of which the edge rays hit the edges 15 of the x-ray image detector 4' or 4".

The ray focus 11 of the x-ray source 3 and the x-ray image detector 4' or 4" in each case run around the object 13 such that the ray focus 11 and the x-ray image detector 4' or 4" lie on opposite sides of the object 13. With the joint movement of x-ray image detector 4' or 4" and ray focus 11 the edge rays of the beam 14' or 14" define a measurement field circle 16' which, if the object 13 extends too far, lies partly or also completely within the object to be examined 13. The measurement field circle 16' of the small detector 4' can have a diameter $r\emptyset=11.8$ cm and measurement field circle 16" of the large detector 4" can have a diameter $\emptyset=24.0$ cm.

An image of the area of the object 13 lying outside the measurement field circle 16' or 16" is thus not formed on the x-ray image detector 4' or 4". As a consequence, under some circumstances truncated projection images of object 13 are recorded by the x-ray image detector 4' or 4". Sectional images of the object to be examined 13 are reconstructed from the truncated projection images by an evaluation unit not shown in the drawing and which is connected downstream from the x-ray image detectors 4' or 4" and for example is arranged in the imaging system 6. The truncated projection images lead in the reconstruction from cross-sectional images positioned in the plane of the beam 14' or 14" of the x-rayed object 13 to truncation artifacts. In particular the image values of the reconstructed cross-sectional image are too high in the edge areas, whereas the image values in the interior of the cross-sectional image by contrast, although lower, are still generally above the actual gray value. Even if the object to be examined 5 attenuates the rays of the outgoing beam 14' or 14" from the x-ray source evenly, an image value profile running transversely across the sectional image thus has a somewhat key shaped curve.

Image values that are too high mean that in the reconstructed cross-sectional image too great an attenuation of the x-rays emitted by the x-ray source 3 through the object 13 will be indicated whereas image values which are too low indicate too little attenuation by the object 13.

In FIG. 3 a complete profile line 20 and a truncated profile line 21 of a simulated row of a Catphan phantom are reproduced, with the projection value pv being plotted over the column index ci. The errors in the sampling can be recognized by comparing these profile lines 20 and 21.

Projection data cut off or truncated in this way generates artifacts in the reconstructed images since the values close to the edges of the image are clearly too high. As a rule the values in the center of the image are also not correctly reconstructed. Such images can thus barely be evaluated for diagnosis, as can be seen with reference to FIGS. 4 and 5, the juxtaposition of which clearly shows the errors occurring during reproduction. FIG. 4 reproduces a reconstructed image making use of the complete projection data. FIG. 5 shows a reconstructed image making use of the truncated projection data. The details to be seen in the inner area are the same. In the center area matches can still be seen. The outer area however appears completely overradiated and nothing can be seen.

The aim of reducing or removing the truncation artifacts has been predominantly approached in literature by supplementing the truncated data in order to obtain the projection profile as would be produced if the measurement field area had encompassed the entire object. The supplementing is done by extrapolation of the truncated data rows. The type of extrapolation differs in the approaches to the solution discussed in the literature.

In "Efficient correction for CT Image artifacts caused by objects extending outside the scan field of view", Med. Phys. 27, Vol. 1, pages 39 to 46, 2000, B. Ohnesorge Et al. [1] describe extrapolation through antisymmetrical mirroring.

In "Reconstruction from Truncated Projections in Cone-Beam CT using Adaptive Detruncation", Paper #1506, RSNA 2003, by K. Sourbelle Et al. [2] a correction of the measurement field overshoot is described in which the truncated projection data is supplemented as consistently as possible. For this purpose an expanded measurement field must first be defined on which the projections are then to be continued. By contrast with similar methods implemented by the manufacturers, expanded consistency criteria are applied here. The image reconstruction itself is undertaken on the expanded measurement field and should truncate at the edge of the physical measurement field.

In C. Penβel Et al. [3] in "Hybrid Detruncation Algorithm for the Reconstruction of CT Data", RSNA paper 2005, the ADT algorithm of [2] has been combined with an iterative method which also uses the data that is to be seen after the reprojection outside the actual measurement field.

An extrapolation method largely proven in practice is the method described in "A novel reconstruction algorithm to extend the CT scan field-of-view", Med. Phys. 31 (9), September 2004, pages 2385 to 2391, by Hsieh Et al. [4], with which truncation artifacts can be suppressed which occur when the object to be examined extends into areas outside the so-called scan field-of-view. The projection images produced in this case are referred to as cut-off or truncated. Truncated projection images generate artifacts when the sectional images are reconstructed. In particular the image values close to the edge in the sectional image are generally too high. The sectional images affected by the truncation artifacts can thus only be evaluated for diagnosis to a limited extent. It is assumed in the method that the "truncated" object is continued by an imaginary circular water cylinder. The cylinder height is the same as the detector height and the radius and the center point position of the circle are to be defined from the projection value and the rise of the projection row at the truncation point, i.e. at the point of the last measured value. As a result of the inevitable noise of the measured values the determination of the rise cannot be numerically robust and can thus produce an incorrect value.

The result is the computation of inappropriate extrapolation values and along with this an inappropriate extrapolation width. An extrapolation width which is too short only incompletely reduces the key-shaped profile of a reconstructed axial section. An extrapolation area which is too large overcompensates for the "key" and leads to a wavy profile section. This means that the outer reconstructed object areas are either increased too far or reduced in value and appear brighter or darker in a gray value representation than the center of the image. A result is the lack of HU fidelity at the object edge and—depending on under or overcompensation—in the center of the image as well.

Further such correction methods are known from J. Sharman Et al. [5] "Extrapolating Truncated Projections Using 0th and 1st Moment Constraints", RSNA 2004, and B. Schulz [6], "Verfahren zur Korrektur von Trunkierungsartifakten" ("Method for correction of truncation artifacts"), older patent application 10 2006 014 629.8.

A method for correcting truncation artifacts is known from DE 103 45 705 A1, with radiation diverging from a radiographic source being emitted and projection images being recorded in different projection directions. In this case an expansion of the projection data by extrapolation is undertaken for each detector row, with the extrapolation width being derived from the projection data of a number of detector rows.

The approaches to the solution mentioned above supplement the truncated data rows one at a time and thus achieve in some cases a significant reduction of the truncation artifacts. The effect of the row-by-row processing however is that the extrapolatory supplementing of the projection data, especially because of noise, can be different from row to row. This would correspond to a supplemented object edge which is unrealistically heavily jagged. This produces non-constant folding data in the column direction which contributes to artifacts on the edge of the image, as can be seen from FIG. 6 for example. FIG. 6 shows an extrapolated projection image which has been created from collimated projection data of a cone-beam phantom. The "fraying" shows the different extrapolation widths resulting from the noise for each row.

An underlying object of the invention is to embody a method of the type mentioned at the start so as to avoid jagged edges when supplementing the edge of the object during extrapolations.

The object is achieved in accordance with the invention by the signal of a projection data row being smoothed with a polynomial filter to reduce the noise component of the signal and by the truncated proportion of the projection data row being computed from the smoothed signal of the projection data row by means of an extrapolation method, with the extrapolation widths being derived from a number of rows.

This truncation correction with cross-row adaptation of the extrapolations means that a jagged object edge is not produced during the supplementing of the projection data rows.

It has proved advantageous for the digitally smoothing polynomial filter to be a Savitzky-Golay filter, especially a second-order digital Savitzky-Golay filter, which can have a filter length corresponding to the number of the extrapolated rows.

In an advantageous manner the following steps can be executed after row-by-row extrapolation of a truncated projection image:

a) The left-side or right-side extrapolation widths are recorded as functions of the row index and stored in a data field, and b) Filtering of the functional areas which are not equal to zero and c) Determination of the filtered curve values as new extrapolation widths and corresponding row-by-row adaptation of the extrapolation widths, which can be followed by the following further steps:

d) Also taking into account during adaptation of the extrapolation widths of a projection image the extrapolation widths of the same row of the adjacent projection images with the same angle.

Inventively the following steps can be executed:

S1 Radioscopy of an object under examination,

S2 Recording of projection images,

S3 Extrapolation of the projection data rows,

S4 Smoothing by filtering of the projection data rows,

S5 Deriving the extrapolation widths from a number of projection data rows,

S6 Extrapolation of the projection data rows and

S7 Reconstruction of sectional images.

BRIEF DESCRIPTION OF THE DRAWINGS

Embodiments of the invention are explained below in greater detail on the basis of the exemplary embodiments shown in the drawing. The figures show.

DETAILED DESCRIPTION OF INVENTION

Figure 7:
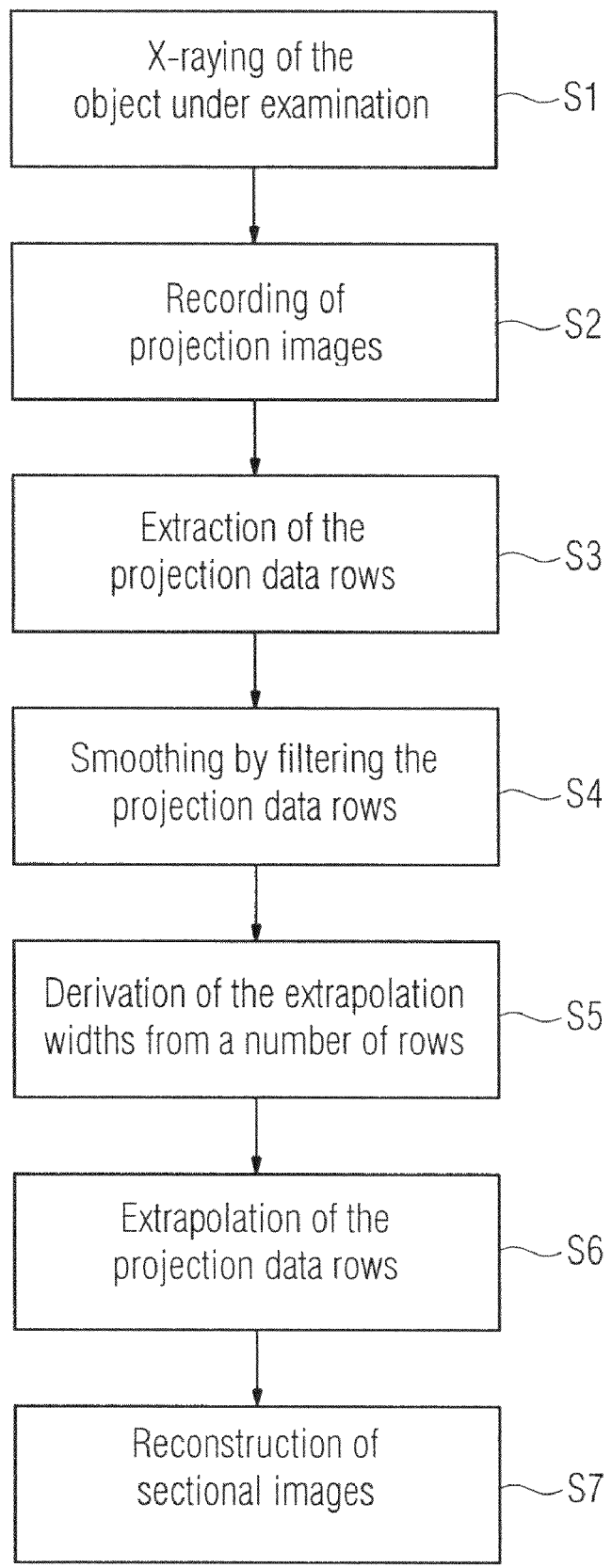

The general execution sequence of the method is now described in greater detail with reference to FIG. 7. The first step S1 involves x-raying the object under examination, of which a recording of projection images is created in the second step S2. As a next step S3 an extraction of the projection data rows is undertaken, of which the result is smoothed in step S4 by filtering the projection data rows. In step S5, by deriving the extrapolation widths from a number of projection data rows, an extrapolation width averaged over a number of rows is determined for each row. In the subsequent step S6 an extrapolation of the projection data rows is undertaken covering the extrapolation widths determined in step S5. In the last step S7 sectional images are reconstructed from the projection data rows and their expansion extrapolated via the widths determined in step S5.

Figure 1:
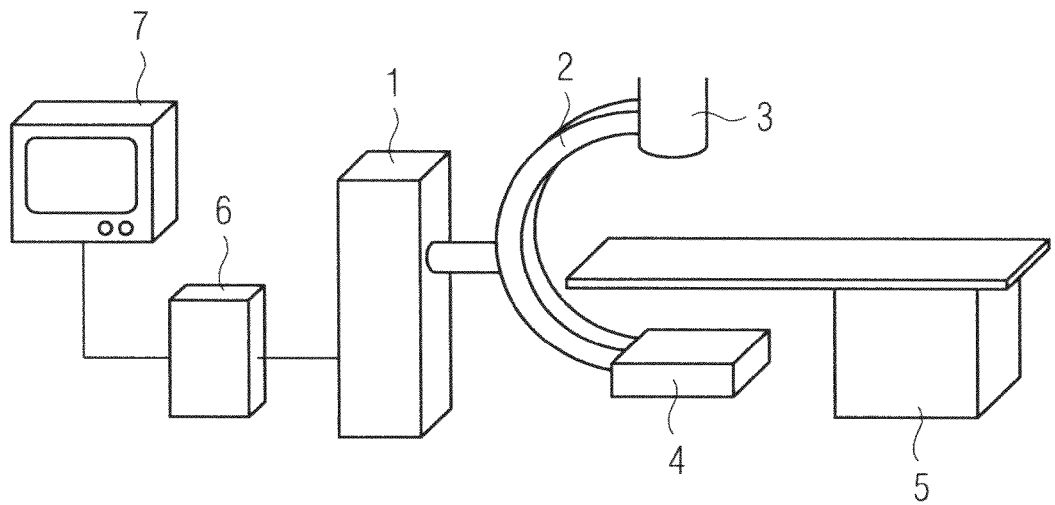
FIG. 1 an x-ray diagnostic device for executing the method.
Figure 2:
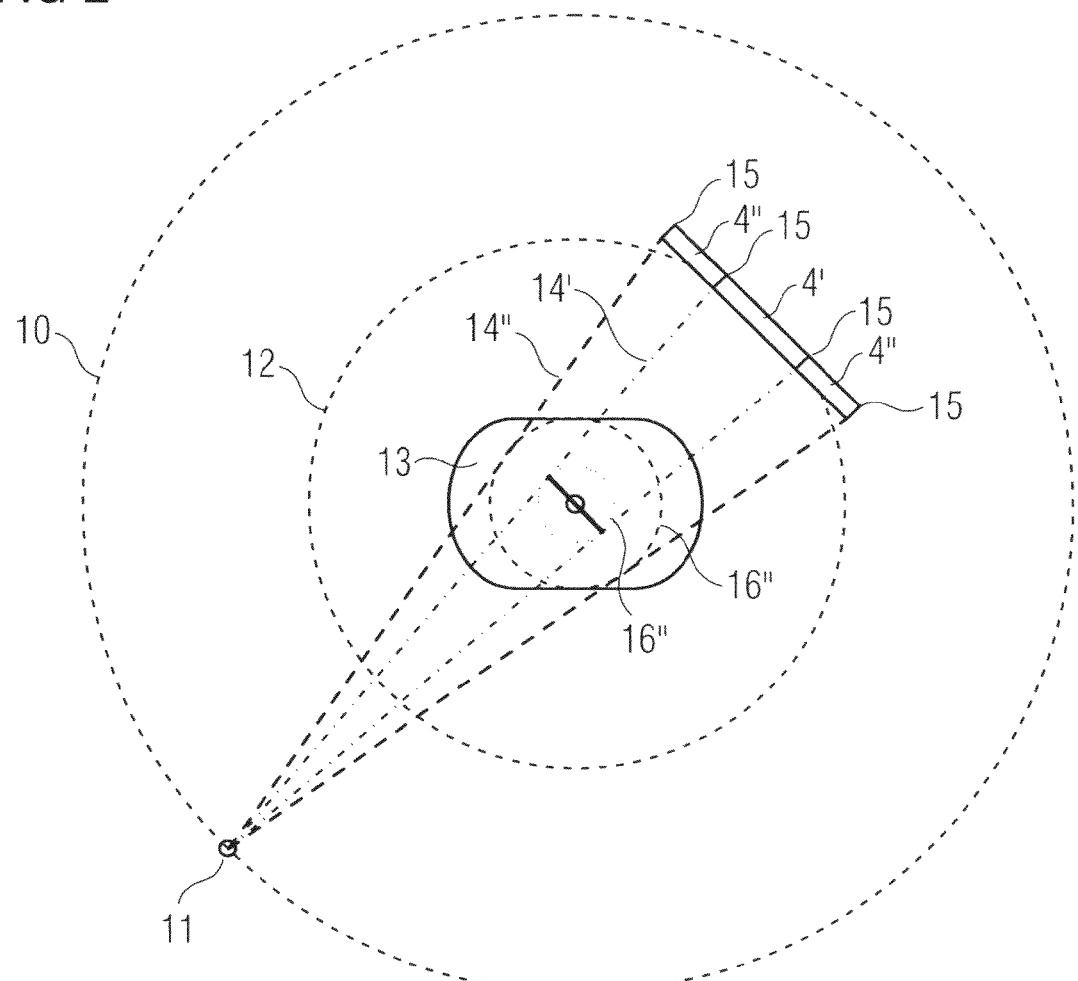
FIG. 2 a view of the measurement geometry with the path of a detector and a radiographic source around a measurement object to be examined in an axial direction of view, FIG. 3 complete and truncated profile lines of a simulated row of a phantom, FIG. 4 a reconstructed image using the complete projection data, FIG. 5 an image reconstructed from truncated projection data, FIG. 6 an extrapolated projection image in accordance with a known method, FIG. 7 the execution sequence of the inventive method, FIG. 8 determined extrapolation widths as function of the row and FIG. 9 an extrapolated projection image in accordance with the inventive method.
Figure 3:
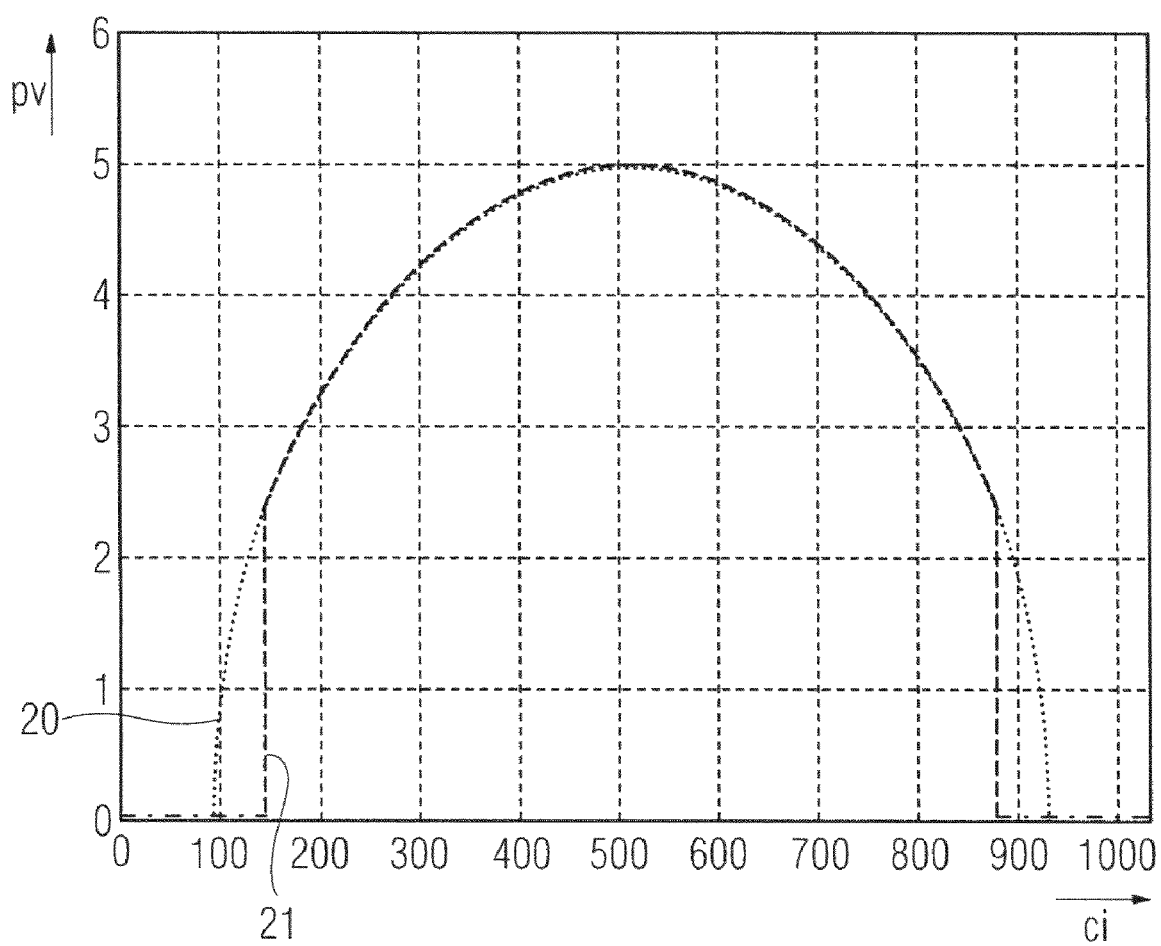
Figure 4:
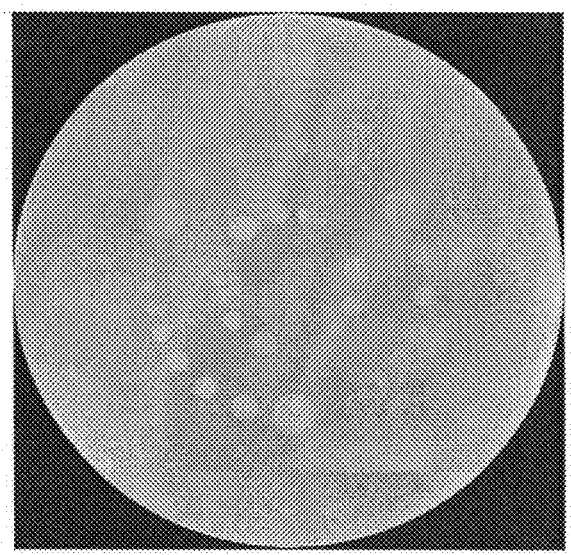
Figure 5:
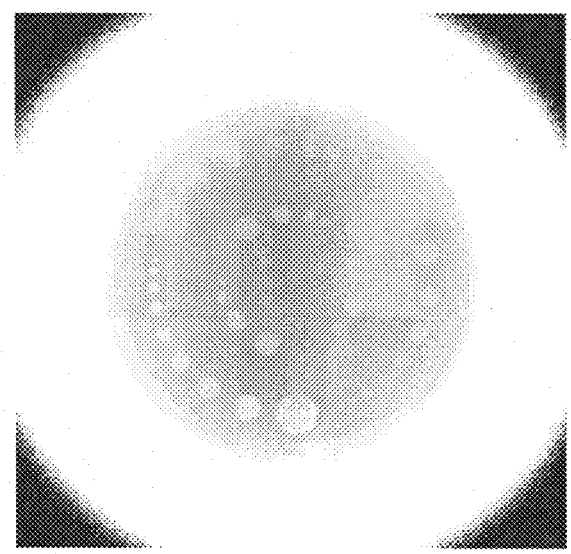
Figure 6:
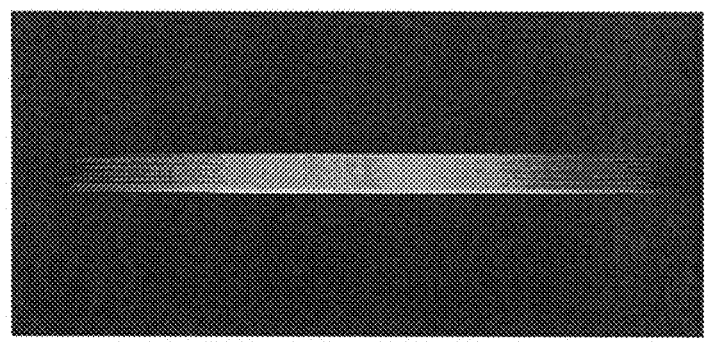
Figure 8:
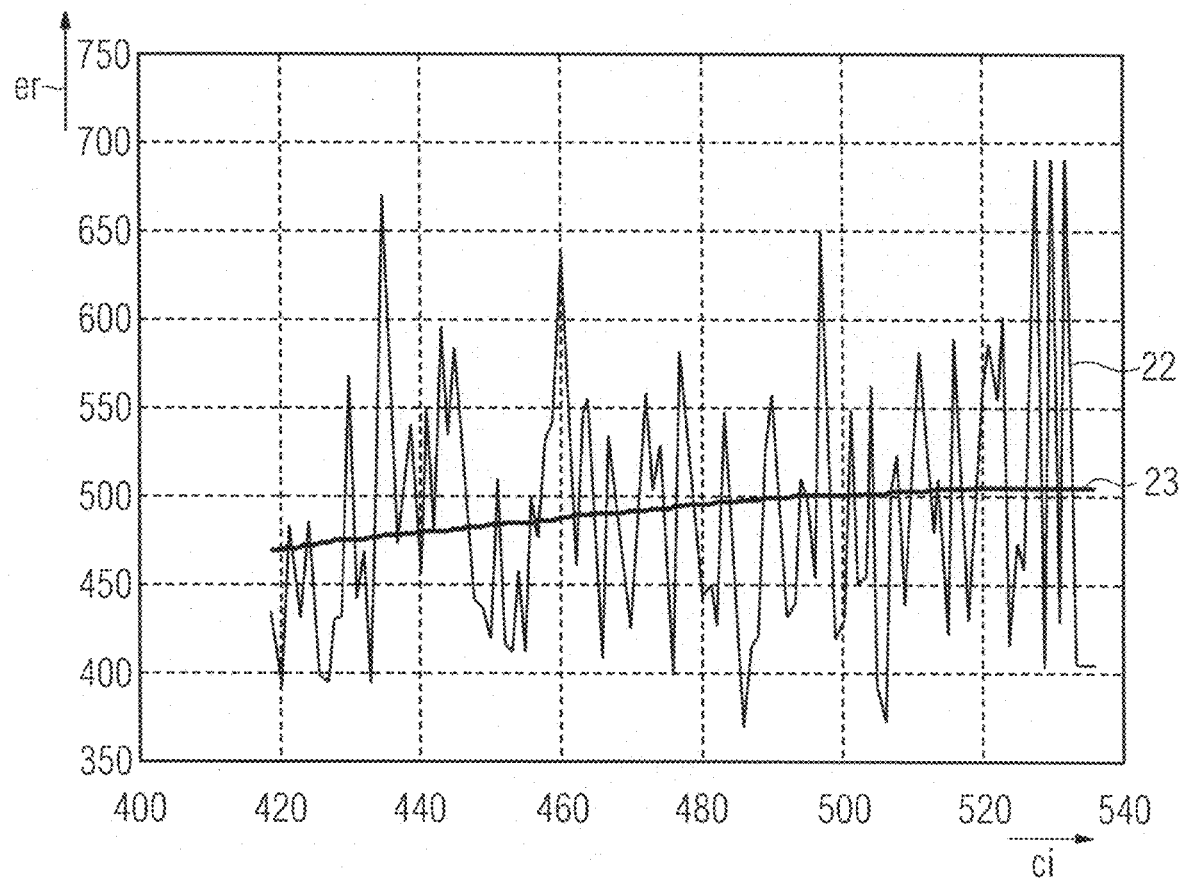

FIG. 8 shows the extrapolation widths 22 of the left side of the x-ray image detector 4 as a function of the row, with the extrapolation range er being plotted over the column index ci. A so-called cone-beam phantom has been used, which produces a collimation to an average contrast slice. The curve varying between extrapolation widths 22 of 370 to 710 illustrates what was only able to be seen as an indication in FIG. 6—the different lengths of the extrapolation for recordings in accordance with the prior art. The second curve shows the cross-row filter result 23—the filtering of the extrapolation widths 22 by means of a second-order Savitzky-Golay filter, with the filter length being equal to the number of the extrapolated lines.

Figure 9:
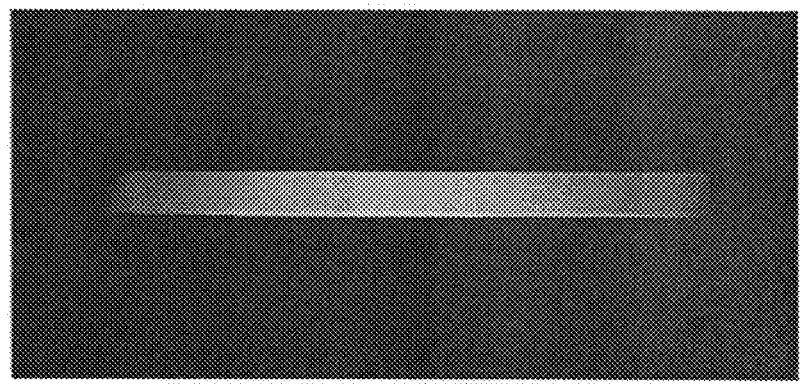

FIG. 9 shows an extrapolated projection image with cross-row filtered extrapolation widths 23, which was created from collimated projection data of a cone-beam phantom. Comparing FIG. 9 to FIG. 6 clearly shows that there are now no jagged edges produced because of noise-related different extrapolation widths for individual rows.

In an embodiment features of the proposed solution can consist of, after row-by-row extrapolation of a truncated projection image 1. Capturing the left-side and right-side extrapolation widths as functions of the row index and storing them in a data field, and
2. Filtering out function areas not equal to zero, and
3. Viewing the filtered curve values as new extrapolation widths and adapting the extrapolation widths row-by-row accordingly, and
4. Where necessary also taking account in the adaptation of the extrapolation widths of a projection image of the extrapolation widths of the adjacent projection images at the same angle.

The even extrapolation along the column direction of the detector, as a rule along the vertical axis of the patient's body, leads to an improved image quality in the edge area of reconstructed 3D volumes of areas of tissue of interest.

Within the framework of the invention, instead of the stand 1 shown, floor-mounted or ceiling-mounted tripods can also be used, to which the C-arms 2 are attached. The C-arm 2 can also be replaced by a so-called electronic C-arm 2, in which x-ray source 3 and x-ray image detector 4 are coupled electronically.

The C-arms 2 can also be guided on robot arms which are attached to the ceiling or the floor. The method can also be executed with x-ray devices in which the individual image-creation components 3 and 4 are held by a robot arm in each case, which are arranged on the ceiling and/or floor.

LITERATURE

[1] B. Ohnesorge, T. Flohr, K. Schwarz, J. P. Heiken, and K. T. Bae, "Efficient correction for CT Image artifacts caused by objects extending outside the scan field of view", Med. Phys. 27, Vol. 1, pages 39 to 46, 2000

[2] K. Sourbelle, M. Kachelrieβ, W. A. Kalender, "Reconstruction from Truncated Projections in Cone-Beam CT using adaptation Detruncation", Paper #1506, RSNA 2003

[3] C. Penβel, M. Kachelrieβ. K. Sourbelle, W. A. Kalender, "Hybrid Detruncation Algorithm for the Reconstruction of CT Data", RSNA paper 2005

[4] J. Hsieh, E. Chao, J. Thibault, B. Grekowicz, A. Horst, S. McOlash, and T. J. Myers, "A novel reconstruction algorithm to extend the CT scan field-of-view", Med. Phys. 31 (9), 2385-2391, September 2004

[5] J. Starman, N. Pelc, N. Strobel, R. Fahrig, "Extrapolating Truncated Projections Using 0th and 1st Moment Constraints," RSNA 2004

[6] B. Scholz, "Verfahren zur Korrektur von Trunkierungsartifakten", ("Method for correction of truncation artifacts", older patent application 10 2006 014 629.8 dated Mar. 29, 2006

The invention claimed is:

1. A method for correction of truncation artifacts in reconstructed tomographic images in a reconstruction method for tomographic images with truncated projection data, comprising:

emitting divergent radiation by a radiographic source;

x-raying an object to be examined in different projection directions with the divergent radiation;

detecting the radiation which has passed through the object to be examined by a detector as projection images, with the data of the signal being arranged in a number of projection data rows;

expanding projection images recorded by the detector row-by-row by extrapolation of the projection data rows;

smoothing the signal of a projection data row with a polynomial filter for reducing the noise component of the signal; and determining the truncated proportion of the projection data row from the smoothed projection data row based upon an extrapolation method, with the extrapolation widths being derived from a number of projection data rows.

2. The reconstruction method as claimed in claim 1, wherein the smoothing polynomial filter is a digital filter.

3. The reconstruction method as claimed in claim 2, wherein the smoothing polynomial filter is a Savitzky-Golay filter.

4. The reconstruction method as claimed in claim 3, wherein the smoothing polynomial filter is a second-order digital Savitzky-Golay filter.

5. The reconstruction method as claimed in claim 2, wherein the smoothing polynomial filter is a second-order digital Savitzky-Golay filter.

6. The reconstruction method as claimed in claim 2, wherein the smoothing polynomial filter is a second-order digital Savitzky-Golay filter with a filter length corresponding to the number of the extrapolating projection data rows.

7. The reconstruction method as claimed in claim 2, further comprising
- x-raying an object under examination,
- recording of projection images,
- extrapolation of the projection data rows,
- smoothing by filtering the projection data rows,
- deriving the extrapolation widths from a number of projection data rows,
- extrapolation of the projection data rows and
- reconstruction of sectional images.

8. The reconstruction method as claimed in claim 1, wherein the smoothing polynomial filter is a Savitzky-Golay filter.

9. The reconstruction method as claimed in claim 8, wherein the smoothing polynomial filter is a second-order digital Savitzky-Golay filter.

10. The reconstruction method as claimed in claim 8, wherein the smoothing polynomial filter is a second-order digital Savitzky-Golay filter with a filter length corresponding to the number of the extrapolating projection data rows.

11. The reconstruction method as claimed in claim 8, further comprising
- x-raying an object under examination,
- recording of projection images,
- extrapolation of the projection data rows,
- smoothing by filtering the projection data rows,
- deriving the extrapolation widths from a number of projection data rows,
- extrapolation of the projection data rows and
- reconstruction of sectional images.

12. The reconstruction method as claimed in claim 1, wherein the smoothing polynomial filter is a second-order digital Savitzky-Golay filter.

13. The reconstruction method as claimed in claim 12, wherein the smoothing polynomial filter is a second-order digital Savitzky-Golay filter with a filter length corresponding to the number of the extrapolating projection data rows.

14. The reconstruction method as claimed in claim 12, further comprising
- x-raying an object under examination,
- recording of projection images,
- extrapolation of the projection data rows,
- smoothing by filtering the projection data rows,
- deriving the extrapolation widths from a number of projection data rows,
- extrapolation of the projection data rows and
- reconstruction of sectional images.

15. The reconstruction method as claimed in claim 1, wherein the smoothing polynomial filter is a second-order digital Savitzky-Golay filter with a filter length corresponding to the number of the extrapolating projection data rows.

16. The reconstruction method as claimed in claim 15, further comprising
- x-raying an object under examination,
- recording of projection images,
- extrapolation of the projection data rows,
- smoothing by filtering the projection data rows,
- deriving the extrapolation widths from a number of projection data rows,
- extrapolation of the projection data rows and
- reconstruction of sectional images.

17. The reconstruction method as claimed in claim 1, wherein after the row-by-row extrapolation of a truncated projection image the left-side or right-side extrapolation widths are recorded as functions of the row index and stored in a data field, the functional areas which are not equal to zero are filtered and the filtered curve values are determined as new extrapolation widths wherein extrapolation widths are adapted row-by-row correspondingly.

18. The reconstruction method as claimed in claim 17, wherein during adaptation of the extrapolation widths of a projection image, the extrapolation widths of the same row of the adjacent projection images with the same angle are also taken into account.

19. The reconstruction method as claimed in claim 17, further comprising
- x-raying an object under examination,
- recording of projection images,
- extrapolation of the projection data rows,
- smoothing by filtering the projection data rows,
- deriving the extrapolation widths from a number of projection data rows,
- extrapolation of the projection data rows and
- reconstruction of sectional images.

20. The reconstruction method as claimed in claim 1, further comprising
- x-raying an object under examination,
- recording of projection images,
- extrapolation of the projection data rows,
- smoothing by filtering the projection data rows,
- deriving the extrapolation widths from a number of projection data rows,
- extrapolation of the projection data rows and
- reconstruction of sectional images.

* * * * *